(12) United States Patent
Hancock et al.

(10) Patent No.: US 11,799,206 B2
(45) Date of Patent: Oct. 24, 2023

(54) HELICAL ANTENNA STRUCTURE

(71) Applicant: CREO MEDICAL LIMITED, Chepstow (GB)

(72) Inventors: Christopher Paul Hancock, Bath (GB); Malcolm White, Chepstow (GB); Patrick Burn, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 989 days.

(21) Appl. No.: 16/082,182

(22) PCT Filed: May 19, 2017

(86) PCT No.: PCT/EP2017/062199
§ 371 (c)(1),
(2) Date: Sep. 4, 2018

(87) PCT Pub. No.: WO2017/198869
PCT Pub. Date: Nov. 23, 2017

(65) Prior Publication Data
US 2019/0081403 A1    Mar. 14, 2019

(30) Foreign Application Priority Data
May 20, 2016   (GB) ..................................... 1608872

(51) Int. Cl.
*A61B 18/00* (2006.01)
*H01Q 11/08* (2006.01)
(Continued)

(52) U.S. Cl.
CPC ........... *H01Q 11/08* (2013.01); *A61B 18/042* (2013.01); *A61B 18/1815* (2013.01);
(Continued)

(58) Field of Classification Search
CPC ... A61B 18/042; A61B 18/1815; A61B 18/18; A61B 2018/00589; A61B 2018/1846;
(Continued)

(56) References Cited

U.S. PATENT DOCUMENTS 3,083,364 A   3/1963  Scheldorf
3,573,681 A *  4/1971  Miller ....................... H01P 3/13
                                                    333/242
(Continued)

FOREIGN PATENT DOCUMENTS

EP   2 335 632 A2   6/2011
EP   3 422 981 A2   1/2019
(Continued)

OTHER PUBLICATIONS

International Searched Report for PCT/EP2017/062199 dated Aug. 10, 2017.
(Continued)

*Primary Examiner* — Joanne M Rodden
*Assistant Examiner* — Rachel A. Vierra
(74) *Attorney, Agent, or Firm* — ArentFox Schiff LLP

(57) ABSTRACT

A helical antenna structure for use in an electrosurgical instrument. The helical antenna structure is connectable to inner and outer conductors of a coaxial transmission line, and can act as both a radiating antenna or applicator structure, and also in a mode where an electric field is generated between its electrodes. In this way, the helical antenna structure may be used both for argon plasma coagulation, and deep tissue coagulation, as well as providing means for delivering a fluid, e.g. a therapeutic fluid such as adrenaline. This may be achieved through the use of helically arranged electrodes and a channel for gas to flow. This device is also used to deliver adrenaline and RF/microwave energy.

17 Claims, 14 Drawing Sheets

(51) Int. Cl.
  *A61B 18/04*  (2006.01)
  *A61B 18/18*  (2006.01)
  *H01Q 1/36*  (2006.01)
  *H01Q 1/38*  (2006.01)

(52) U.S. Cl.
  CPC .............. *H01Q 1/362* (2013.01); *H01Q 1/38* (2013.01); *A61B 18/18* (2013.01); *A61B 2018/00589* (2013.01); *A61B 2018/1846* (2013.01); *A61B 2018/1892* (2013.01)

(58) Field of Classification Search
  CPC ........... A61B 2018/1842; H01Q 11/08; H01Q 1/362; H01Q 1/38
  See application file for complete search history.

(56) References Cited

U.S. PATENT DOCUMENTS

| | | | | |
|---|---|---|---|---|
| 4,583,556 | A * | 4/1986 | Hines | A61B 18/1815 607/116 |
| 5,154,705 | A * | 10/1992 | Fleischhacker | A61B 17/3207 600/585 |
| 5,246,438 | A * | 9/1993 | Langberg | A61B 18/1492 600/374 |
| 5,334,193 | A | 8/1994 | Nardella | |
| 5,784,034 | A | 7/1998 | Konishi et al. | |
| 5,909,196 | A | 6/1999 | O'Neill, Jr. | |
| 6,075,501 | A | 6/2000 | Kuramoto et al. | |
| 6,208,903 | B1 * | 3/2001 | Richards | A61B 18/1815 607/101 |
| 2010/0125269 | A1 * | 5/2010 | Emmons | A61B 18/1815 606/33 |
| 2012/0032871 | A1 * | 2/2012 | Leisten | H01Q 1/362 343/895 |
| 2013/0324911 | A1 * | 12/2013 | Ohri | A61M 25/007 606/41 |
| 2015/0223882 | A1 * | 8/2015 | Curley | A61B 18/1815 606/33 |

FOREIGN PATENT DOCUMENTS

| | | |
|---|---|---|
| WO | WO 90/06079 A1 | 6/1990 |
| WO | WO 94/11059 A1 | 5/1994 |
| WO | WO 97/48449 A1 | 12/1997 |
| WO | WO 2004/045442 A1 | 6/2004 |

OTHER PUBLICATIONS

Search Report issued in United Kingdon Application No. GB 1608872.6 dated Jul. 15, 2016.

* cited by examiner

HELICAL ANTENNA STRUCTURE

CROSS-REFERENCE TO RELATED APPLICATIONS

This application is a National Stage entry of International Application No. PCT/EP2017/062199, filed on May 19, 2017, which claims priority to United Kingdom Patent Application No. 1608872.6, filed on May 20, 2016. The disclosures of the priority applications are incorporated in their entirety herein by reference.

FIELD OF THE INVENTION

The invention relates to an antenna structure for use in surgical scoping devices.

BACKGROUND TO THE INVENTION

It is known that microwave energy and radiofrequency (RF) energy can be used to perform coagulation in deep lying tissue, by contacting the site of the bleed with the surgical probe. It is also known that surface bleeding can be controlled in a contactless manner using argon plasma coagulation (APC) whereby a high-energy electric field is applied across a jet of argon gas, in order to ionize the gas and strike a plasma. The plasma is then able to cause coagulation. Vasostrictive fluid to close open bleeding vessels is also often used as an emergency intervention to control blood flow or to stop bleeding prior to the application of a coagulating agent or an alternative means to permanently plug or seal the bleeding vessels.

SUMMARY OF THE INVENTION

At its most general the present invention provides a helical antenna structure which can be connected to the inner and outer conductors of a coaxial transmission line, and which can act as both a radiating antenna or applicator structure, and also in a mode where an electric field is generated between its electrodes. In this way, the helical antenna structure may be used both for APC, and deep tissue coagulation, as well as providing means for delivering a fluid, e.g. a therapeutic fluid such as adrenaline. This may be achieved through the use of helically arranged electrodes and a channel for gas to flow. This device is also used to deliver adrenaline and RF/microwave energy More specifically, the present invention provides a helical antenna structure which can be connected to a coaxial transmission line having an inner conductor and an outer conductor, the helical antenna structure having: a dielectric support, a first helical electrode and a second helical electrode both located on the dielectric support, and electrically isolated from each other, first connection means for connecting the first helical electrode to the inner conductor of a coaxial transmission line; second connection means for connecting the second helical electrode to the outer conductor of a coaxial transmission line; wherein at least one of the first helical electrode and the second helical electrode is able to act as a radiating antenna structure for outwardly emitting a microwave/RF field; and the first helical electrode and the second helical electrode are configured to sustain an electric field in the helical region therebetween to generate displacement current.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz.

The helical configuration of the present invention is able to act as an effective radiative antenna structure, evidence of which is presented later in this application. Such a field can then be used for coagulation. Using helical electrodes ensures that a central region of the antenna structure is not taken up. This means that other structures can pass through the centre of the antenna structure to deliver a fluid or gas, for example adrenaline or saline. The helical antenna structure is preferably configured to be used in conjunction with an endoscope, laparoscope or the like, and accordingly preferably has a maximum outer diameter of no more than 8 mm, preferably equal to or less then 5 mm, and more preferably equal to or less than 3.5 mm, and most preferably no more than 2.5 mm. The dielectric support is preferably substantially cylindrical, and may have a rounded distal end. Having a rounded distal end, rather than a pronounced circular vertex results in a smoother distribution of emitted microwave/RF energy, giving more uniform coagulation. In preferred embodiments there are only two helical electrodes on the outer surface of the dielectric support, but there may also be e.g. three or four helical electrodes.

The dielectric support may comprise one or more of PEEK, PTFE, ceramic or other suitably rigid, low loss material.

The first and second helical electrodes preferably have the same pitch, and may be located diametrically opposite to each other. In other words: in appearance, the second helical electrode runs parallel to the first helical electrode, but at a fixed axial offset, so that coils of the first and second helical electrodes alternate with each other. Most preferably, the first and second helical electrodes are identical to, or substantially identical to each other. The first and second helical electrodes are preferably located on the surface of the dielectric support, or partially embedded therewithin.

In use, the antenna is inserted distal end first, with the distal end surface facing towards the site of a bleed. Therefore, it is preferable that the greatest degree of heating (as a result of microwave/RF energy delivery) should occur at the distal end, and around the outer curved surface of the helical antenna. In this way, effective energy delivery may be achieved by placing the helical antenna either distal end first towards a target area, or on its side. Therefore, it is preferable that microwave/RF energy may be delivered by a waveguide structure or a transmission line structure to the distal end of the helical antenna structure. The transmission line structure may be part of the helical antenna structure itself, or alternatively, the helical antenna structure may have a channel or chamber which is configured to receive a coaxial transmission line structure, or other structure capable of conveying microwave/RF energy to the distal end of the helical antenna structure without an appreciable degree of attenuation. If microwave/RF energy is delivered only to the proximal end of the helical antenna structure, without any transmission line structure to convey it to the distal end, it is likely that attenuation will occur between the proximal end and the distal end as a result of undesirable absorption by tissue which is touching the structure. Using a helical antenna structure as in the present invention means that, for example, a coaxial transmission line from which the first and second helical electrodes are configured to receive microwave/RF energy may pass through the structure all the way to the distal end of the helical antenna structure.

Alternatively, in a preferred embodiment, the first and second helical electrodes are configured to be connected to the inner and outer conductor of a coaxial transmission line having a hollow inner conductor. Accordingly, the dielectric support may have a central channel running through it, terminating in an aperture. In this way, a structure such as a liquid-delivery tube or the like may pass all the way through the helical antenna structure, without causing a detrimental effect on the radiative properties of the antenna structure. Accordingly, it is preferable to leave a central or near-central region of a distal end of the helical antenna structure exposed, and so a liquid-delivery tube, a needle or the like, can be inserted through the end of the helical antenna, in the event that it is necessary to deliver a liquid medication such as adrenaline to a target area. This tube may also be a sealed region (i.e. a space inside the catheter capable of containing a microwave cable, needle activation wire and short length of needle) for fluid to flow. Alternatively, a hollow needle may run from the proximal handle end to the distal end of the device. The bore size of the needle may be 0.4 mm or 0.5 mm, but the invention is not limited to this being the case, i.e. it may be 0.8 mm for a laparoscopic device. The needle may be made from stainless steel or the like. The hollow or needle channel may also be used to deliver gas, for example argon, and the RF field available at the helical antenna may be used to strike plasma, whilst the microwave field may be used to sustain plasma. In this configuration, the gas will need to be present between the radiators that set up and deliver RF and microwave energy. This may be achieved by providing holes in the dielectric cylinder that allow the gas to escape into regions where an electric field exists between the electrodes.

In a preferred embodiment, the helical antenna structure further includes a third helical electrode, which is located beneath the surface of, and preferably embedded within, the dielectric support, and preferably located beneath the first helical electrode, and more preferably runs along the same helical path as the first helical electrode, but radially inwards from it. Accordingly, the first and third helical electrodes also share a longitudinal axis. The first helical electrode may be connected to the inner conductor of a coaxial transmission line at a feed point, and the third helical electrode may be connected to the outer conductor of a coaxial transmission line via a feed point. Then, since the first and third helical electrodes follow the same path, they may act as a continuation of the waveguide structure of the coaxial transmission line, and further convey the signal from the proximal to the distal end of the helical antenna structure.

The first and third helical electrodes, and preferably also the second helical electrode may be in the form of helical strips of conducting material, and therefore the transmission line formed by the first and third helical electrodes may be a microstrip line. Preferably, the width of the strip of conducting material forming the first helical electrode is wider than, and preferably at least double, and more preferably at least triple the width of the strip of conducting material forming the third helical electrode. In this way, it is possible to ensure that there is significant enough overlap between the two helical electrodes that an efficient microstrip line structure is formed. This is because the currents at the edge of the first helical electrode (due to the feed signal) will be low, and will not result in significant interaction with any tissue in contact with the outer surface of the first helical electrode. The microstrip line structure formed by the first helical electrode and the third helical electrode is preferably arranged to have an impedance of approximately 50 Q, in order to be matched with a coaxial transmission line from which the feed points are arranged to receive microwave/RF signals.

At the distal end of the helical antenna structure, the distal ends of the second and third helical electrodes are electrically connected to each other. In this way, the microwave/RF energy which is conveyed along the length of the antenna structure by the microstrip line is able to excite corresponding signals which travel back towards the proximal end of the helical antenna structure, along the helical gaps between the first and second helical electrodes. Preferably, a conductive member which connects the second and third helical electrodes does not obscure the aperture of the central channel.

Rather than having a third helical electrode, in an alternative embodiment, in order to take advantage of the helical structure, the dielectric support may have a channel running all or part of the way through it, in a longitudinal, or substantially longitudinal direction, for receiving a coaxial transmission line which supplies the antenna structure with the microwave/RF energy. The connection means for connecting the first helical electrode and the inner conductor, and/or the second helical electrode and the outer conductor are preferably located towards the distal end of the channel, in order to ensure that maximum heating occurs at the distal end of the helical antenna structure, as discussed above.

The inner and outer conductor of the coaxial transmission line may be connected to the first and second helical electrodes, respectively, by bores in the dielectric support. Preferably, there are two bores, one arranged to connect the first helical electrode and inner conductor, and another to connect the second helical electrode and outer conductor. In use, a coaxial transmission line may be inserted into the channel in the dielectric support, and the bores may be filled with solder in order to provide the requisite electrical connections. In this case, the channel may not extend all the way to the end of the helical antenna structure.

Alternatively, in another embodiment, the channel for receiving the coaxial transmission line may extend all the way to the distal end of the dielectric support. The inner and outer conductor of the coaxial transmission line may be connected to the first and second helical electrode via the aperture at the end of the channel. The aperture is preferably shaped to take advantage of the insulating properties of the dielectric layer separating the inner and outer conductors of the coaxial transmission line. For example, the aperture may be substantially circular, with a radius greater than that of the inner conductor, and less than that of the dielectric layer, and with a tab extending radially to a radius greater than the radius of the dielectric layer. In this way, the outer conductor is only exposed in the region of the tab, and remains covered around the rest of the circumference of the aperture. Then, the second helical electrode may be electrically connected, by solder or otherwise, to the outer conductor only in the tab section, without any undesirable electrical connection to the inner conductor.

In another alternative embodiment, the dielectric support may be in two parts. At the distal end, one part may have a projection, and the other part may have a corresponding recess. Parts of the projection may then be plated with a conducting material, arranged to provide the electrical connections between the inner and outer conductors of the coaxial transmission line and the first and second helical electrodes.

In another embodiment, the dielectric may contain holes or slots, preferably between the conductors in the helix, to allow gas to be present in the region between the conductors to allow plasma to be stuck, using the RF field, and sustained, using the microwave field.

BRIEF DESCRIPTION OF THE DRAWINGS

The invention will now be described with reference to the accompanying drawings, in which:

FIGS. 10A, 10B, 11A, 11B, 12A and 12B show alternative configurations of how a coaxial transmission line may be connected to first and second helical electrodes in a helical antenna that is an embodiment of the invention.

DETAILED DESCRIPTION OF THE EMBODIMENTS

Figure 1A:
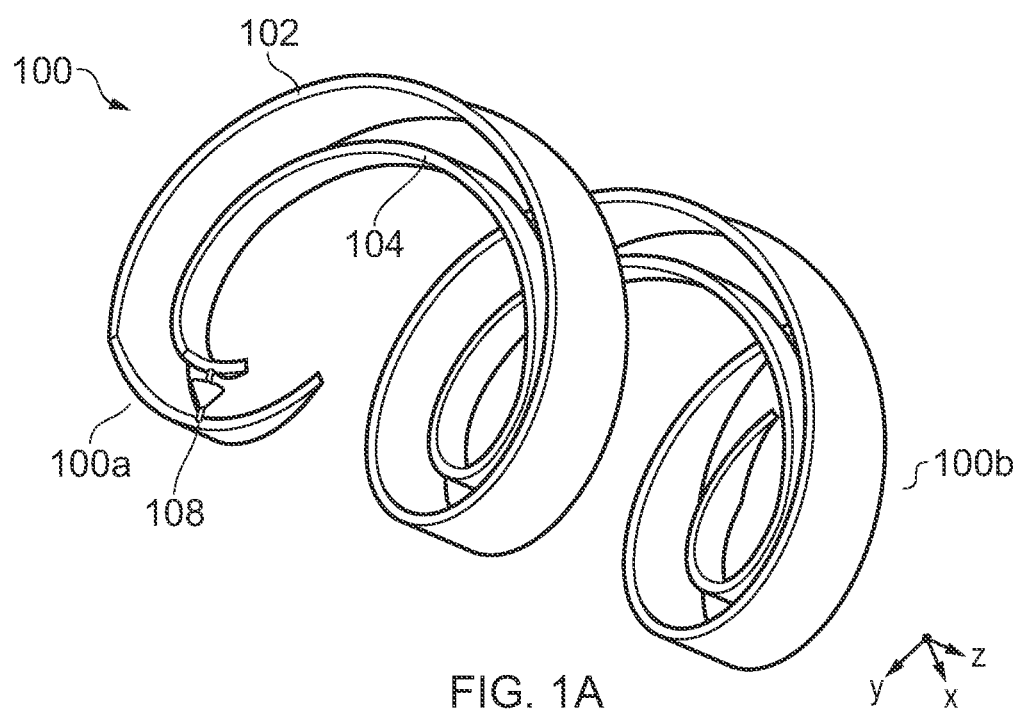
FIG. 1A shows an arrangement of the inner helical electrode and the first outer helical electrode according to an embodiment of the present invention.

FIG. 1A is a view showing the proximal end of a helical antenna 100, which may form the first and second electrodes, and conducting structure of the present invention. In the drawing, the direction from the proximal end 100a to the distal end 100b of the helical antenna is parallel to the z-axis, as shown in the bottom right corner of the drawing.

A first outer helical electrode 102 and an inner helical electrode 104 are shown in FIG. 1A. The inner helical electrode 104 has the same pitch as the first outer helical electrode 102, and has a smaller diameter, so that it runs directly beneath it, and parallel to it. The proximal ends of the two helical electrodes 102, 104 are fed with microwave/RF energy from the coaxial transmission line at the feed point 108, shown by the line and cone. The first outer helical electrode 102 and the inner helical electrode 104, together, form a helical microstrip transmission line, with an impedance of 50 Q (in the presence of an alumina dielectric, see description of drawings below).

Figure 1B:
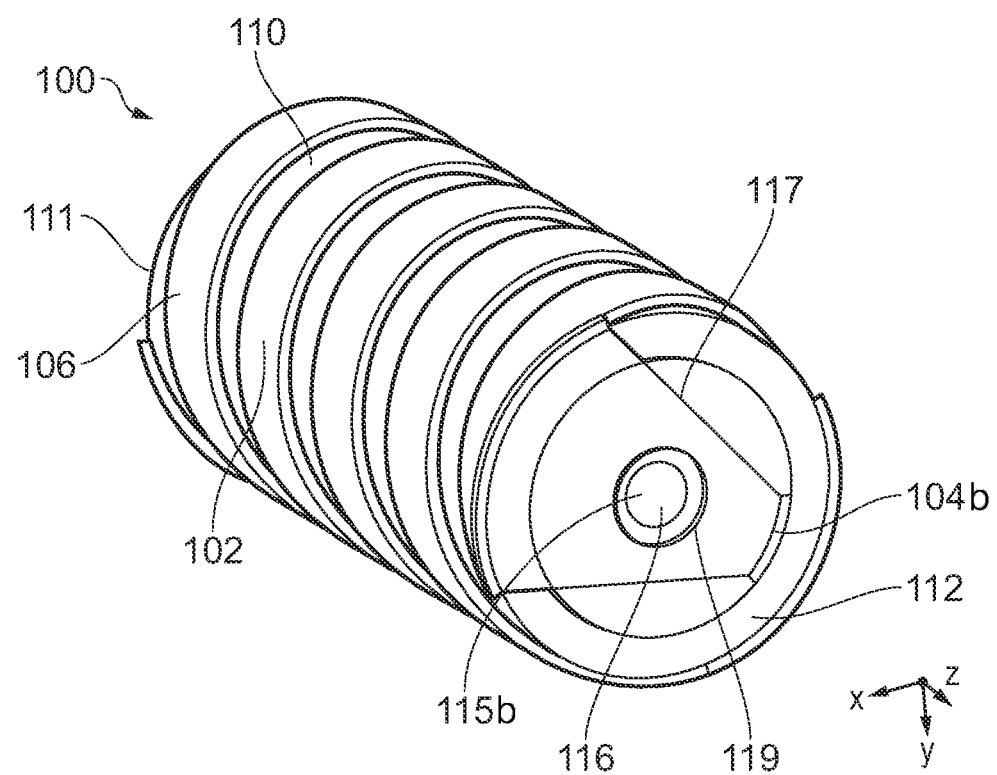
FIG. 1B shows an example of a helical antenna, including a dielectric support, according to an embodiment of the present invention.

FIG. 1B shows a view of a probe tip 111 having the helical antenna 100 supported thereupon. The probe tip 111 consists of a cylindrical dielectric material 112, which in this case is alumina, having a cylindrical bore through it, forming a central channel 115 which runs from a proximal end to a distal end in the z-direction as shown. The central channel terminates at its distal end 115b in aperture 116. The aperture is unimpeded so that a liquid channel (not shown) or other tool can pass through the probe tip 111 for use on a target area (also not shown).

In addition to the first outer helical electrode 102 and the inner helical electrode 104, a second outer helical electrode 106 is also supported on the dielectric material 112. The second outer helical electrode 106 is diametrically opposite to the first outer helical electrode 102, but has identical pitch. In FIG. 1B, the first and second outer helical electrodes 102, 106 and the inner helical electrode 104 have a pitch of 3.3 mm. Only a distal end surface of the inner helical electrode 104b is visible in FIG. 1B, since inner helical electrode 104 is embedded within the dielectric material 112, running directly beneath the first outer helical electrode 102. At the distal end of the dielectric material 112, the distal end of the second outer helical electrode 106 and the distal end of the inner helical electrode 104 are connected by connecting member 117. The connecting member 117 is a disc shaped piece of conducting material, e.g. copper, which has a hole 119 in the centre to coincide with the aperture 116, in order that it remains unimpeded.

In operation, microwave/RF energy is fed into the proximal end of the helical microstrip transmission line formed by the first outer helical electrode 102 and the inner helical electrode 104. When the microwave/RF energy reaches the distal end, a microwave/RF signal is excited between the first and second outer helical electrodes and propagates back, towards the distal end of the probe tip 111 along a helical path through the gaps 110 between the first and second outer helical electrodes 102, 106. When the probe tip 111 is connected to a coaxial transmission line having a gas channel located around it (not shown) e.g. in a jacket spaced from the coaxial transmission line, the first and second outer helical electrodes 102, 106 and the gaps therebetween 110 lie in the flow path of gas exiting the gas channel. When an electric field is present between the first and second outer helical electrodes 102, 106 as a result of the microwave/RF signals propagating along them, the electric field acts to ionize the gas and generate a plasma.

Figure 2:
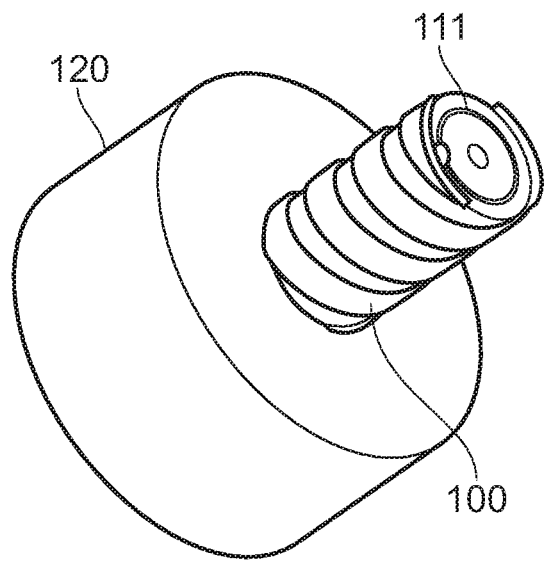
FIG. 2 shows an arrangement of a helical antenna and a liver load which is used to run a simulation of an embodiment of the present invention.

FIG. 2 shows a model used to simulate the effect of a helical antenna 100 as shown in FIGS. 1A and 1B when placed end-on against a liver load 120. The dielectric material 112 in the model is alumina ceramic, a strong, non-porous dielectric with good dielectric breakdown properties. The dielectric constant is 9.4, and its loss tangent is 0.0004 at 5.8 GHz, which represents a very low loss material at the microwave frequencies employed. A copper helix (i.e. helical antenna 100) was modelled on the outside of a 3.3 mm diameter alumina cylinder which is 7.5 mm long. The pitch of the helix is 3.3 mm, and the width of the copper, measured in a direction parallel to the axis of the cylinder is 0.9 mm. The copper strips in the model shown are 0.1 mm thick, but in practice could be as thin as 0.003 mm. A second copper helix was modelled diametrically opposite (i.e. rotated 180') from the first copper helix. This resulted in two inter-wound copper helices with a 0.75 mm gap therebetween (in the direction parallel to the axis of the cylinder).

The inside diameter of the alumina cylinder (i.e. the diameter of the probe tip channel) was 2.5 mm. A 2.3 mm diameter inner alumina cylinder was modelled inside this, with a 0.6 mm diameter hole in the centre, with a 0.5 mm diameter steel needle inside it. An inner copper helix was modelled on the inner alumina cylinder which was 0.35 mm wide in the axial direction, and also having a pitch of 3.3 mm. The inner copper helix is located exactly under the centre of the width of one of the outer copper helices.

The distal end of the inner copper helix was connected to the distal end of the copper helix under which it does not directly lie.

The helical antenna made up by the three copper helices was fed with a 500 feed at its proximal end, between the inner helix and the first copper helix, and a termination between the proximal ends of the two outer helices. A liver load was created and used to determine the power absorption around the tool, which gives an indication of the expected coagulation patterns which may be achieved by using the tool in this way. In the simulation shown, the distal end of the probe tip is inserted 2 mm into the liver load.

Figure 3A:
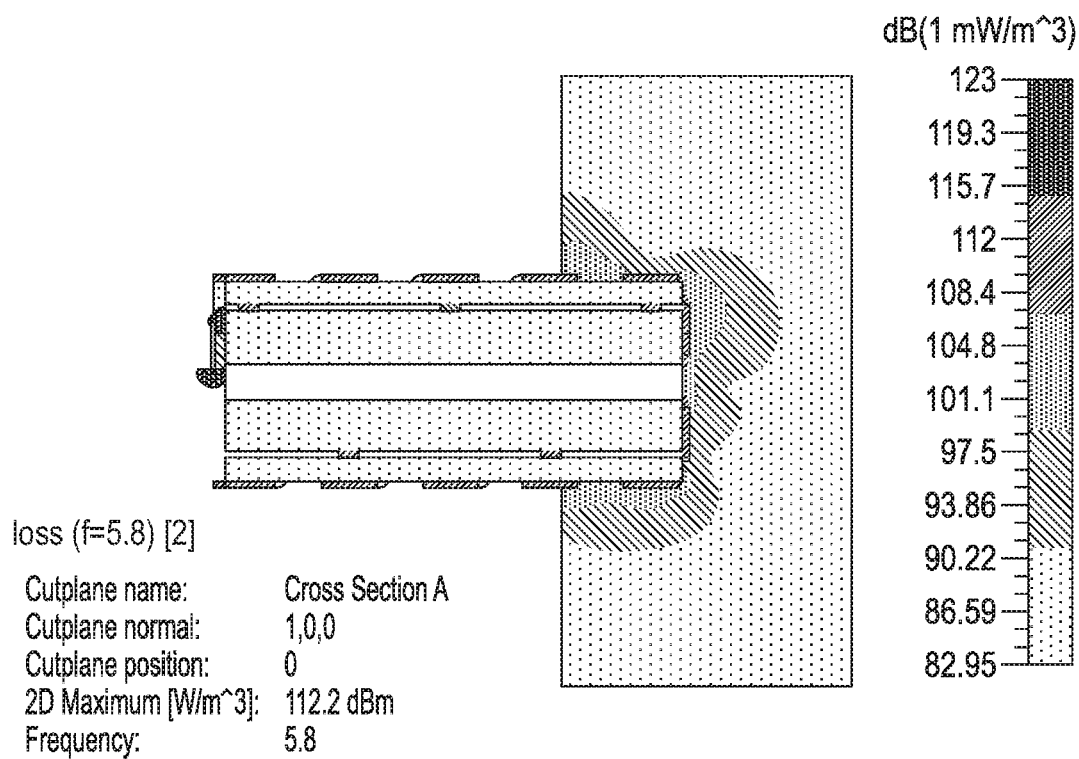
FIGS. 3A, 3B, 3C and 3D show various results of the simulation shown in FIG. 2.
Figure 3B:
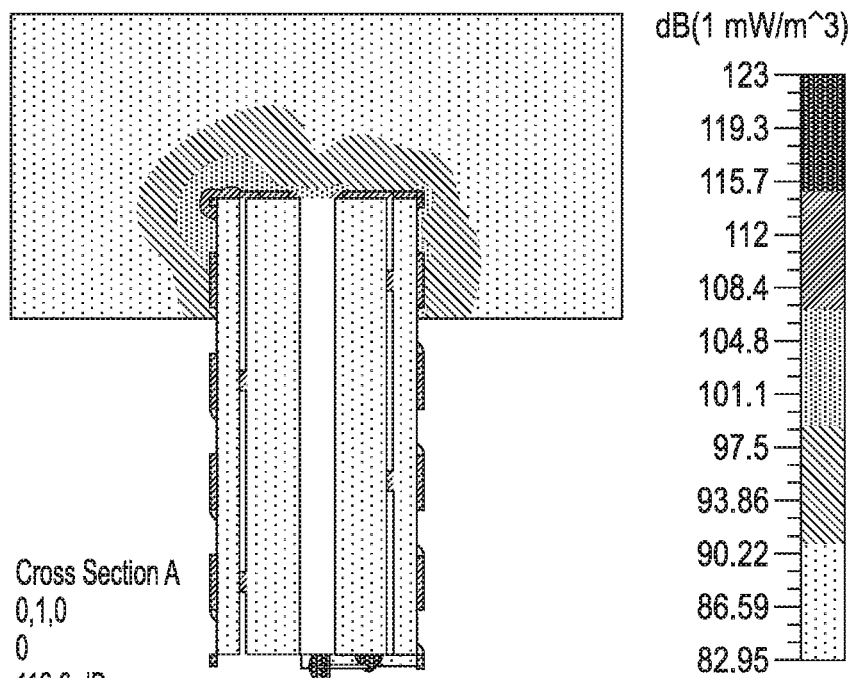
Figure 3C:
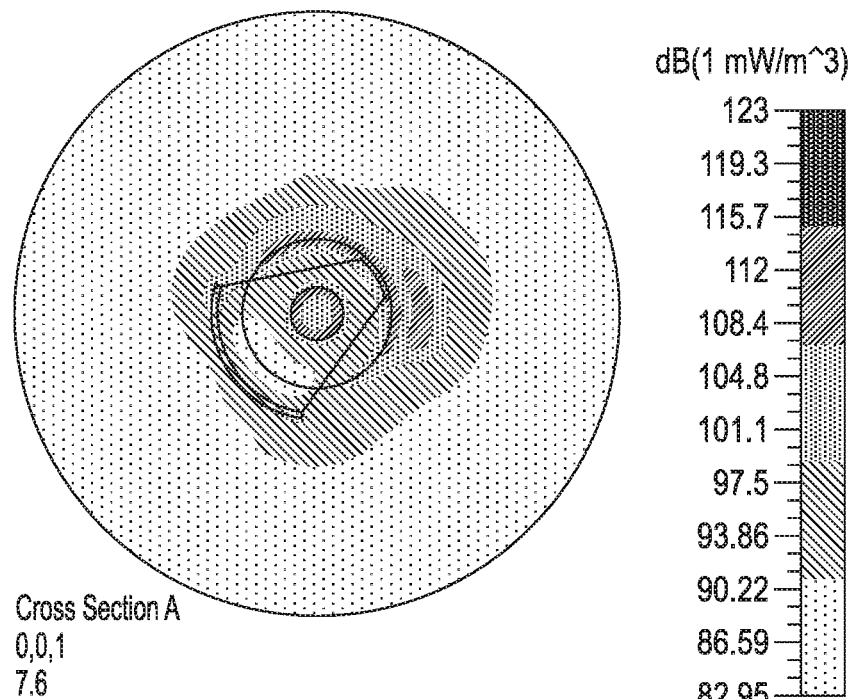
Figure 3D:
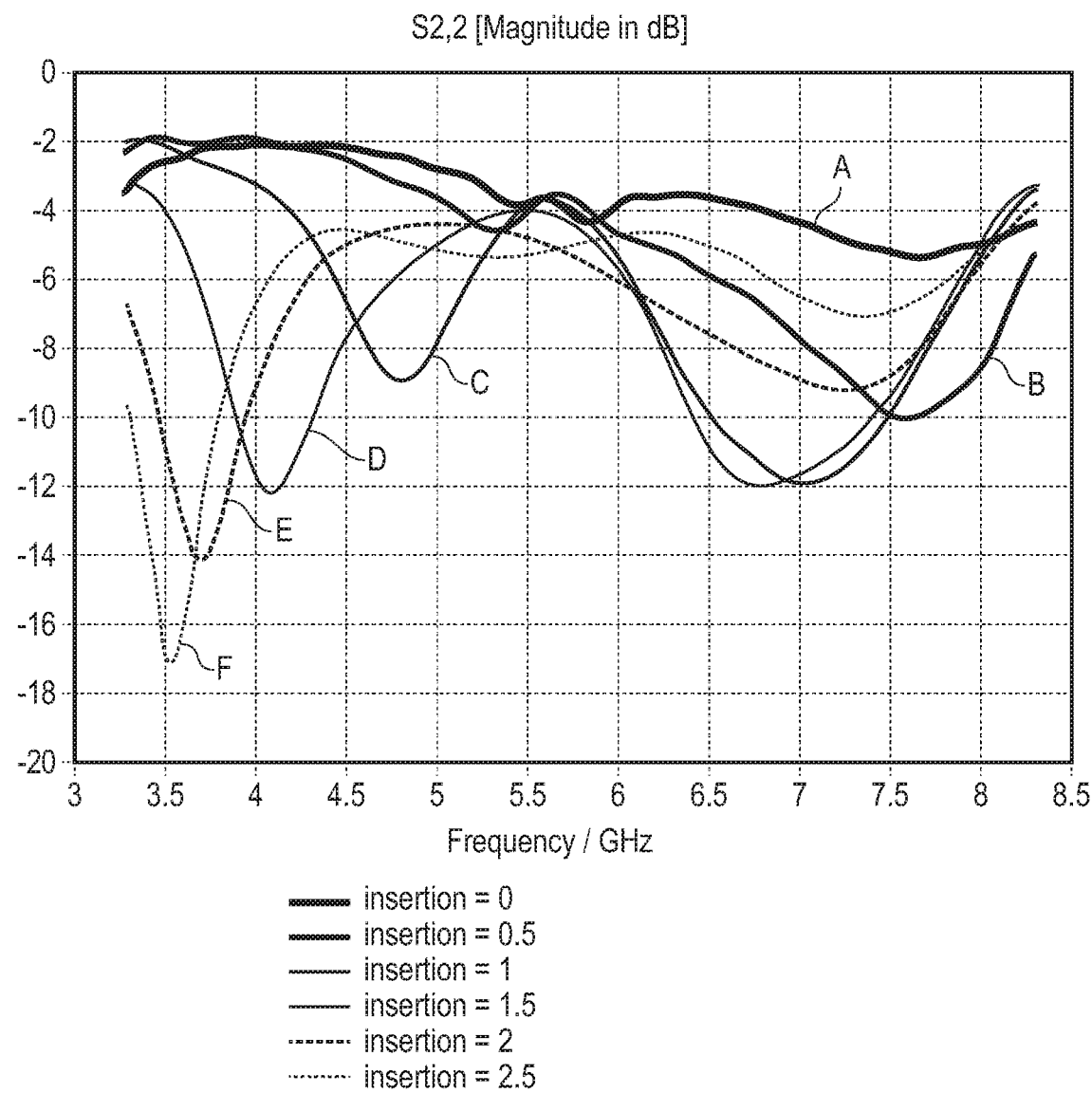

FIGS. 3A to 3C show plots of the power absorption in the liver load around the distal end of the probe tip as shown in FIG. 2 in three different orientations, two taking lengthwise cross sections of the probe tip, and one taking an axial cross section. Overall, these plots show that between 60 and 70% of the microwave power is absorbed into the liver load. FIG. 3D shows the results of simulations of return loss at different penetration depths of the probe tip into the liver load. At 5.8 GHz, it can be seen that the return loss improves from 4 to 5 dB as the insertion increases from 0 (Line A) to 2.5 mm (Line F).

Figure 4:
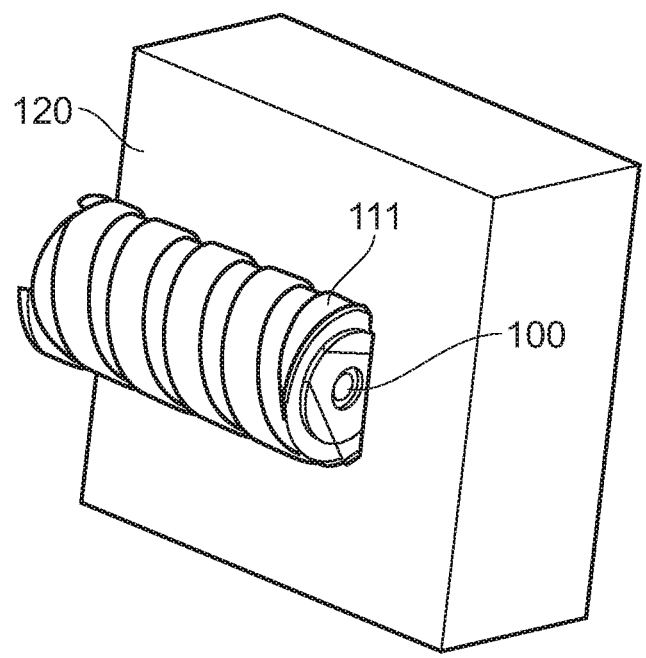
FIG. 4 shows another arrangement of a liver load and helical antenna which is used to run an alternative simulation of an embodiment of the present invention.
Figure 5A:
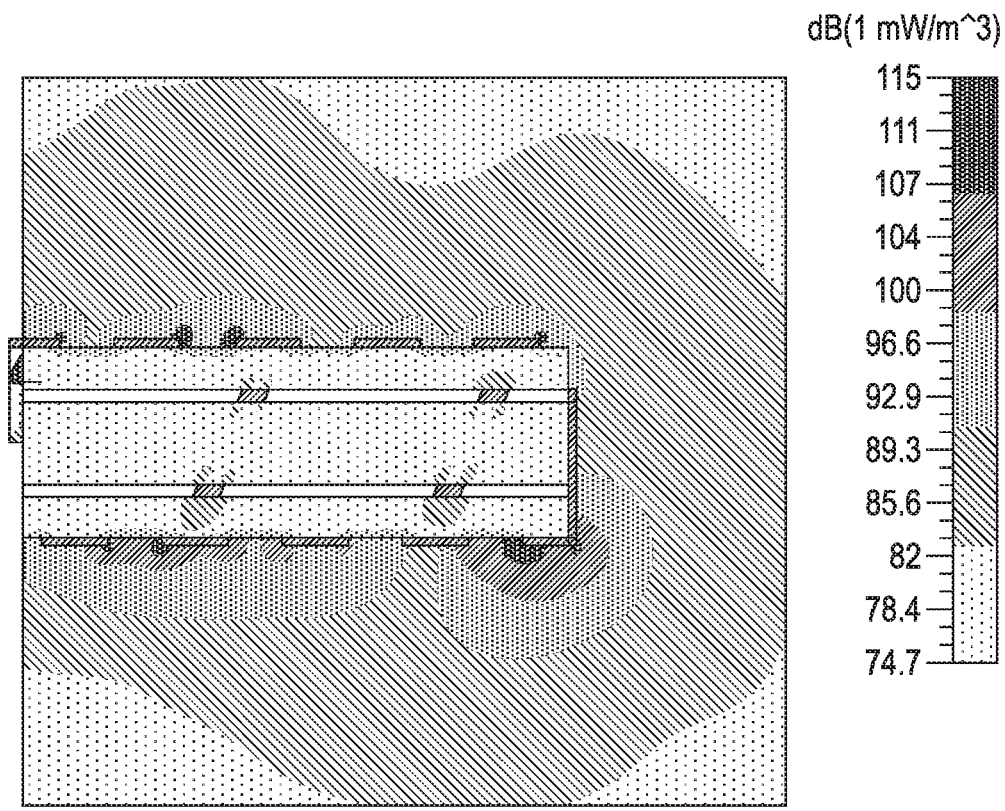
FIGS. 5A, 5B, 5C and 5D show various results of the simulation shown in FIG. 4.
Figure 5B:
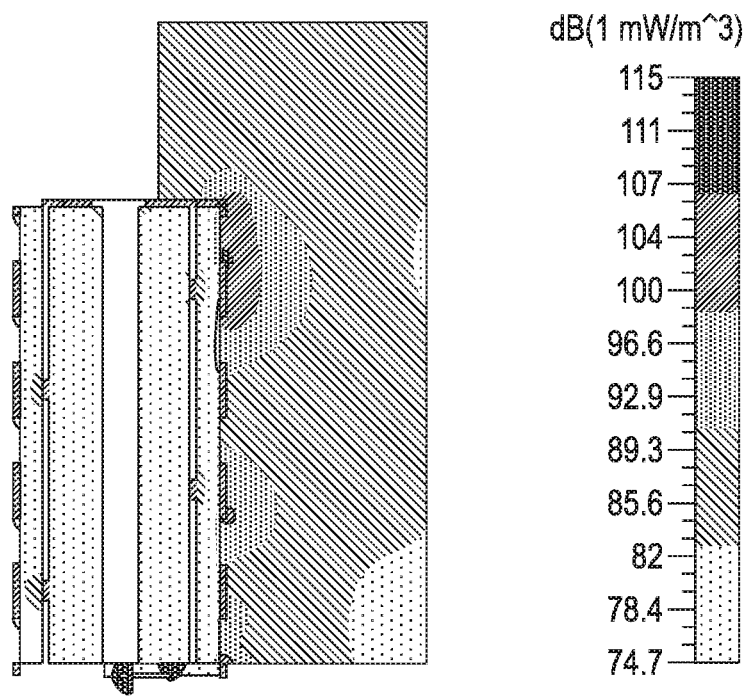
Figure 5C:
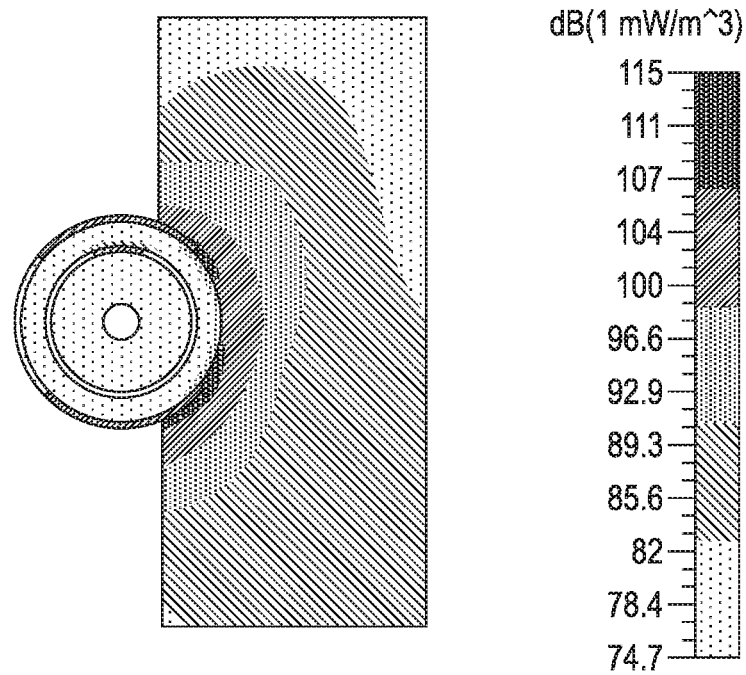
Figure 5D:
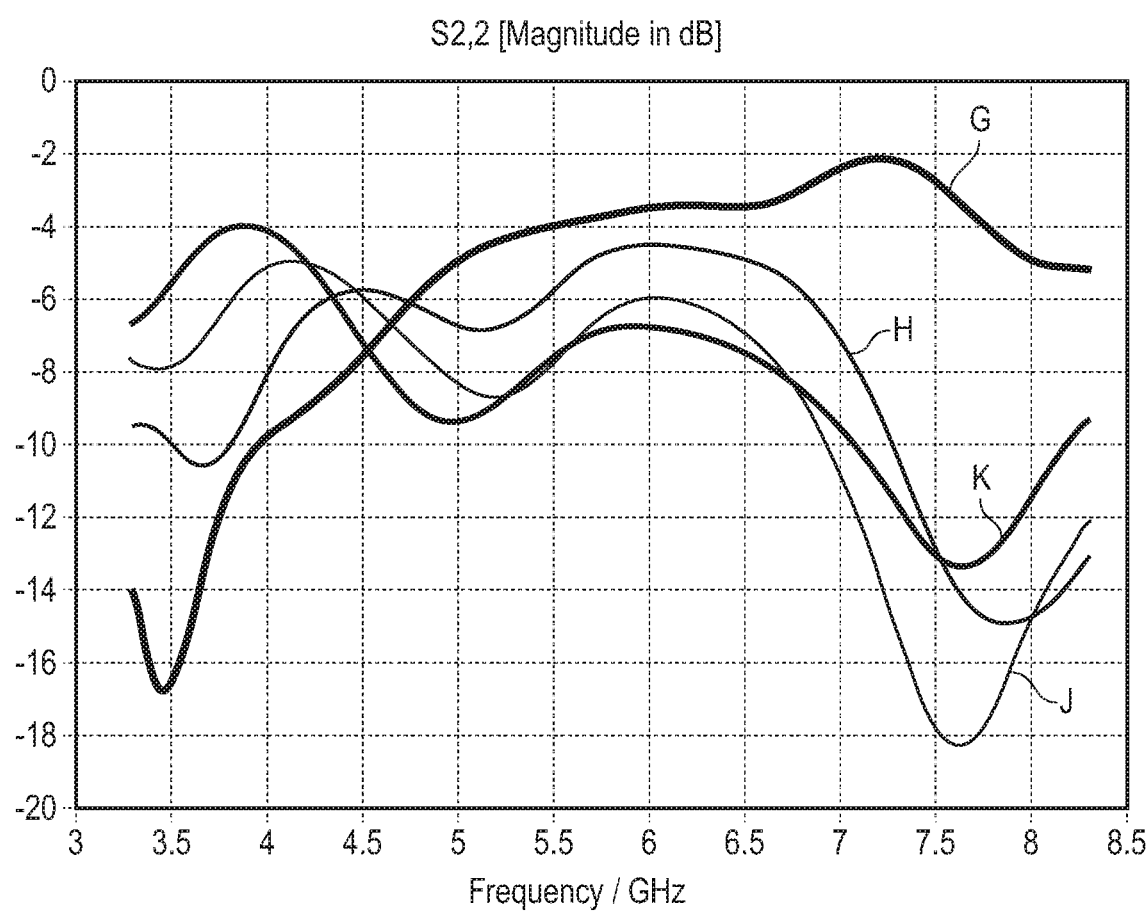

FIG. 4 shows the setup of an alternative simulation, wherein the probe tip is inserted side-on by 1 mm into an identical liver load as in FIG. 2. FIGS. 5A to 5C show plots of the power absorption in the liver load around the probe tip when placed side-on to the liver load. These plots show that the helical antenna is able to produce a substantially even microwave field around the probe tip. FIG. 5D shows the results of simulations of return loss at different penetration depths of the probe tip into the liver load. At 5.8 GHz, it can be seen that the return loss improves from 4 to 7 dB as the (sideways) insertion increases from 0 (Line G) to 1.5 mm (Line K).

The results from the side-on and end-on placement of the helical antenna 100 show that the helical antenna 100 is able to operate effectively as a microwave emitting antenna structure, in addition to being able to strike and sustain a plasma in the helical gaps between the first and second outer helical electrodes.

Figure 6A:
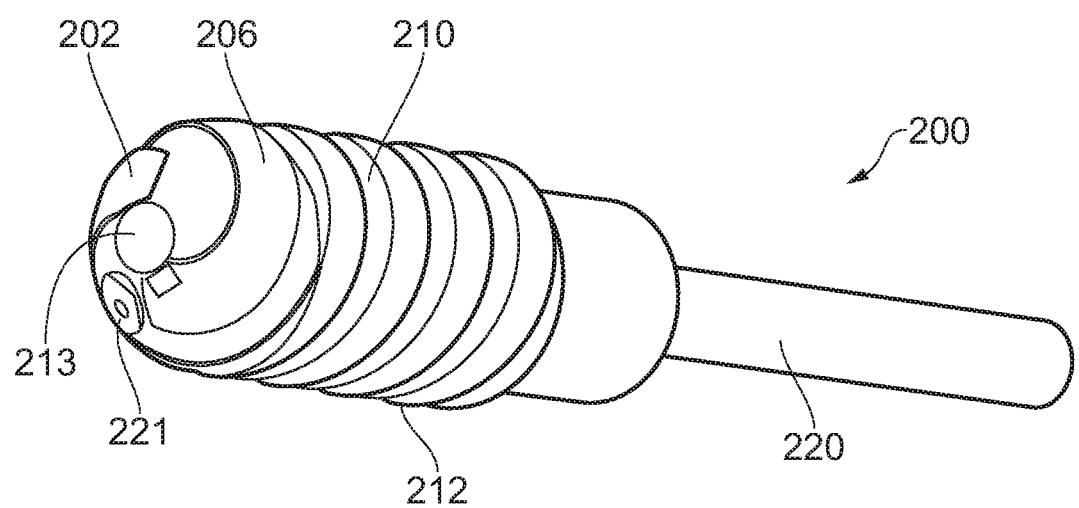
FIG. 6A shows a perspective of a helical antenna that is another embodiment of the present invention.
Figure 6B:
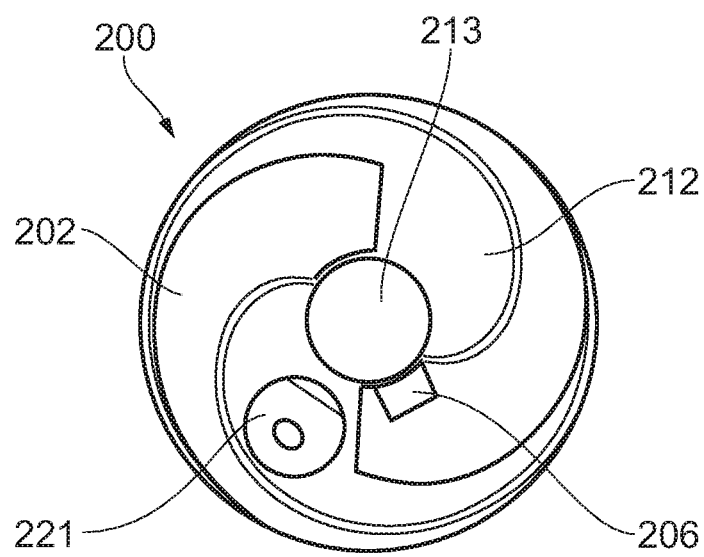
FIG. 6B is an end view of the helical antenna of FIG. 6A.

FIGS. 6A and 6B shows an alternative embodiment of a helical antenna 200 according to the present invention. There are several similarities between the helical antenna 200 of FIG. 6A, and the helical antenna 100 in e.g. FIG. 1B. Where features are identical, they will not be described again in detail.

Helical antenna 200 includes dielectric material 212, which in this case is PEEK, and can be divided into a cylindrical portion, and a hemispherical portion, integrally formed with each other. The outer diameter of the helical antenna structure 200 in this embodiment is 3.3 mm. Channel 215 runs through the centre of both portions of the dielectric material 212, for receiving coaxial transmission line 220. The first and second helical electrodes 202, 206 are connected to the inner and outer conductors of the coaxial transmission line 220 via metal plating extending into the aperture (not shown). For protection, an insulating plug 213 is placed over the connections. This arrangement is shown in more detail in FIGS. 11A and 11B, and discussed below. Dielectric material 212 also has an off-axis needle channel 221 running through it, for situations where it is necessary also to dispense liquid to a target area. Two outer helical electrodes 202, 206 are located on the surface of the dielectric material 212. In use, a coaxial transmission line 220 is inserted through the channel of the helical antenna structure 200. FIGS. 10A, 10B, 11A, 11B, 12A and 12B show different examples of the geometry of the dielectric material 212, each illustrating a different means by which a coaxial transmission line may be connected to each of the helical electrodes 202, 206.

In FIGS. 10A, 10B, 11A, 11B, 12A and 12B, the electrodes 202, 206 are not shown. To connect a coaxial transmission line using the dielectric body 300 of FIGS. 10A and 10B, the coaxial transmission line 320 is embedded along the central channel. The coaxial transmission line 320 must be stripped to expose, successively, as shown in the drawing, the outer conductor 320a, the dielectric layer 320b and the inner conductor 320c The dielectric body 300 shown in FIGS. 10A and 10B has two holes 322a, 322b drilled through it. When the coaxial transmission line 320 is inserted, one of the holes 322a intersects with the exposed inner conductor 320c, and the other hole 322b intersects with the exposed outer conductor 320a. Then, the holes can be filled with solder, to establish an electrical connection and to secure the coaxial transmission line 320 in place.

Figure 11A:
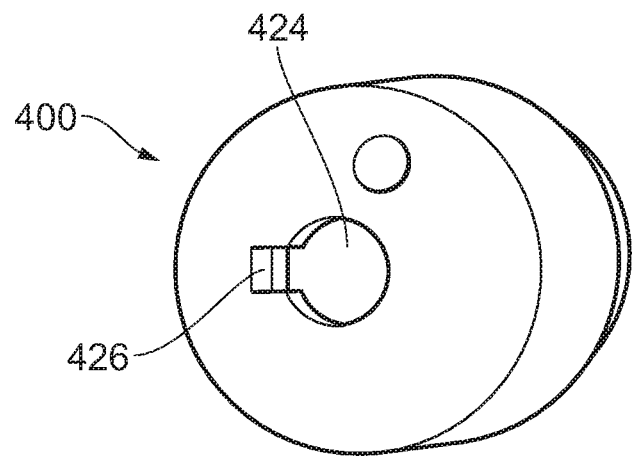
FIG. 11A is an end view of a dielectric body suitable for use with a helical antenna according to another embodiment of the invention.
Figure 11B:
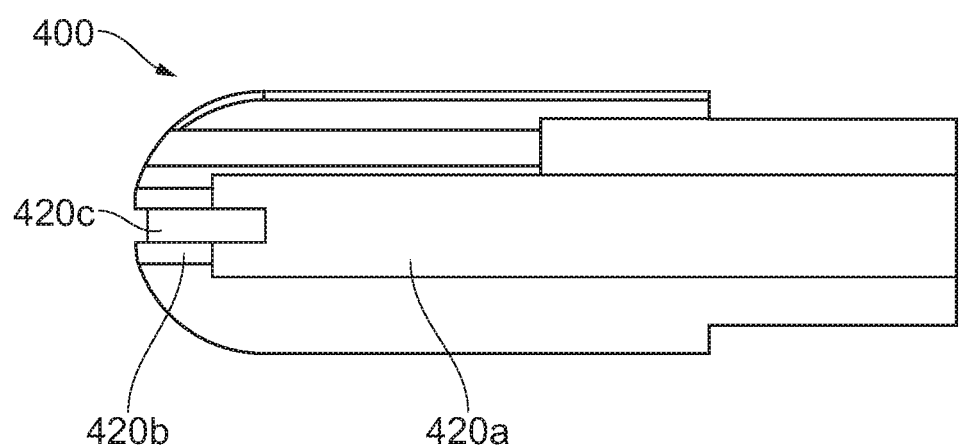
FIG. 11B is a cross-sectional view of the dielectric body shown in FIG. 11A.

In FIGS. 11A and 11B, the coaxial transmission line extends all the way to the distal end of the dielectric body 400. In this embodiment, the outer conductor 420a of the coaxial transmission line is stripped back to expose the dielectric layer 420b. The dielectric layer 420b and the inner conductor 420c then continue to the end of the dielectric body 400, and are exposed at the hole 424, shown best in FIG. 11A. A tab 426 is located at the edge of the hole 424. When the coaxial transmission line is in place, the end surface of the outer conductor 420a is exposed by the tab 426. Importantly, it is electrically isolated from the inner conductor 420c, by the barrier formed by the intervening dielectric layer 420b. As shown in FIG. 11B, the inner conductor 420c of the coaxial transmission line may be recessed. The tab 426 may be filled with solder, and the solder connected to one of the helical electrodes 202, and the recess may be filled with solder (which does not contact the solder in the tab 426) and the solder connected to the other of the helical electrodes 206. Though not shown, as discussed above, metal plating may be used to connect the conductors of the coaxial cable to the helical electrodes, and the recess defined by the inner surface of the hole and the end surface of the coaxial transmission line may be filled with an insulating plug.

Figure 12A:
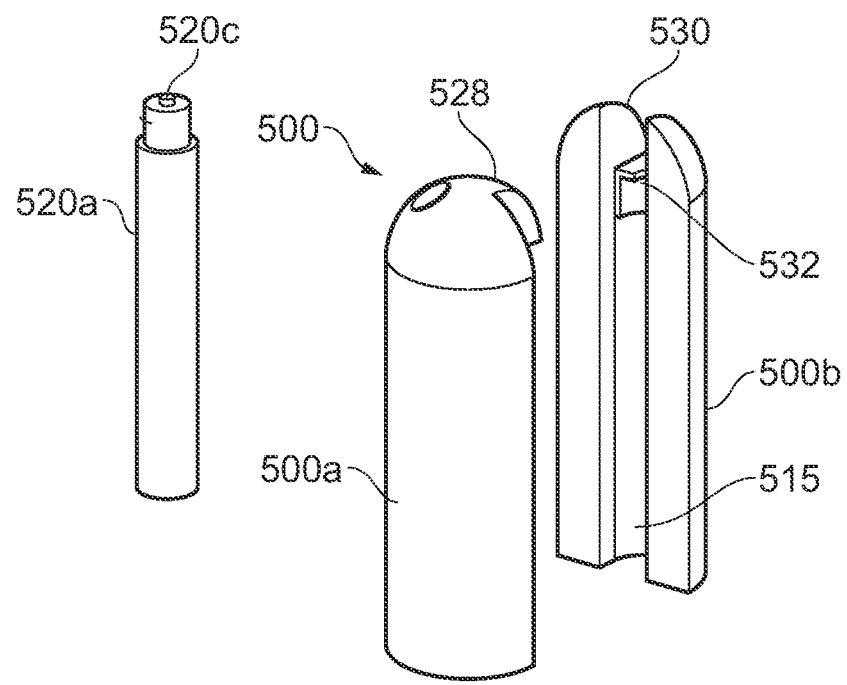
FIG. 12A is an exploded perspective front view of a dielectric body and coaxial cable suitable for use with a helical antenna according to another embodiment of the invention.
Figure 12B:
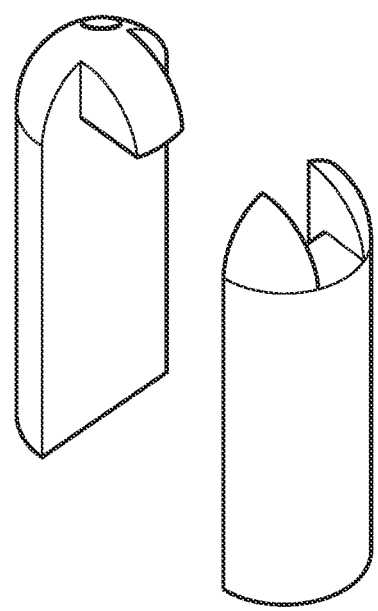
FIG. 12B is an exploded perspective rear view of the dielectric body of FIG. 12A.

A further alternative is shown in FIGS. 12A and 12B. In this case, the dielectric material formed 500 is formed in two pieces 500a, 500b, which are joined together to form helical antenna structure. The first piece 500a has projection 528, which corresponds to a recess 530 on second piece 500b. The second piece 500b also has a channel 515 for receiving the coaxial cable 520. When in place, the base of the recess 530 covers only around half of the upper surface of the coaxial transmission line 520, and leaves half exposed. The base of the recess 530 has a notch 532 to receive the inner conductor 520c of the coaxial transmission line 520. Then, the surfaces indicated by the arrows in FIG. 12B can be plated with conducting material, the conducting material extending to the hemispherical surface 512b of the dielectric material 512, in order to connect the inner conductor 520c and outer conductor 520a to their respective helical electrodes 202, 206.

Referring back now to FIGS. 6A and 6B, the operation of the device will be described. The operation is similar to that of the embodiment of the invention which is shown in FIGS. 1A and 1B. The primary difference between the two embodiments is that in the present embodiment, a coaxial transmission line (e.g. 320) is connected directly to the first helical electrode 202 and the second helical electrode 206, whereas in the previous embodiment, the microwave/RF energy was transferred to the distal end of the helical antenna structure 200 by the microstrip transmission line formed by the helical electrodes 102, 104.

In helical antenna structure 200 shown in FIGS. 6A and 6B, coaxial transmission line 220 is connected to, and conveys microwave/RF energy to the helical electrodes 202, 206 as described above. Since a potential difference exists between the first helical electrode 202 and the second helical electrode 206, an electric field exists in the helical gaps 210 between the first helical electrode 202 and the second helical electrode 206. If this field is high enough, and the gaps are placed in a gas flowpath, then this can cause a plasma to be struck in the helical gaps 210. This means that the helical antenna structure can be employed in APC mode. Furthermore, due to its geometry, the helical antenna structure is also capable of acting as a radiating antenna for radiating microwave/RF energy outwardly, for deep-tissue coagulation. A needle may also be inserted through the off-axis needle channel 221.

Figure 6C:
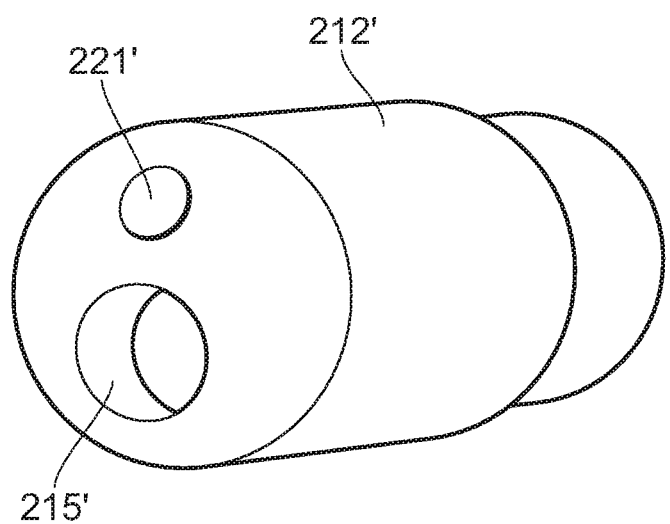
FIG. 6C is a perspective view of a dielectric body suitable for use with a helical antenna according to an embodiment of the invention.

In a similar embodiment, shown in FIG. 6C, the outer diameter of the dielectric material 212' is only 2.4 mm, and both the channel 215' and the needle channel 221' are located off-axis. A dielectric material 212' having this geometry is equally suitable for connecting to a coaxial transmission line using the same internal arrangements as shown in FIGS. 10A, 10B, 11A, 11B, 12A and 12B.

Figure 7:
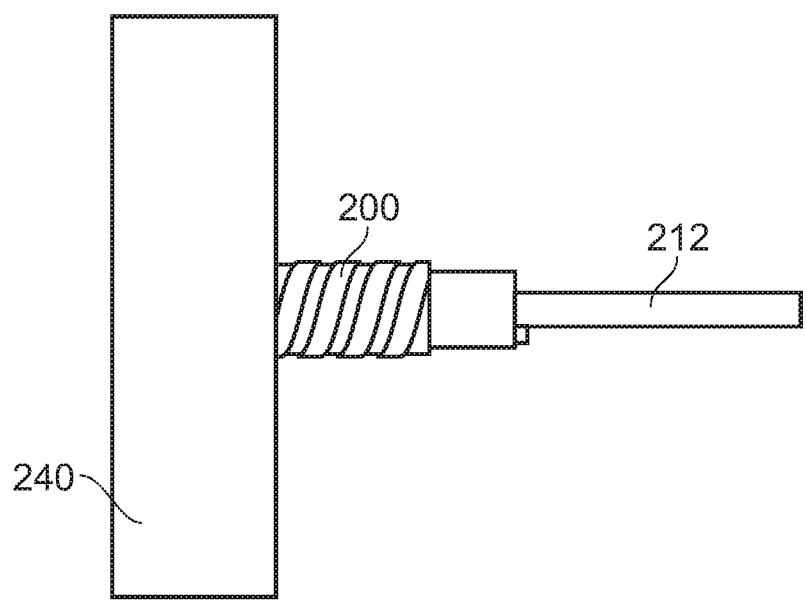
FIG. 7 shows an arrangement of a helical antenna as shown in FIGS. 6A and 6B, and a blood load, which is used to run a simulation of that embodiment.

FIG. 7 shows a testing arrangement used to test the performance of the helical antenna 200 shown in FIGS. 6A and 6B, when acting as a microwave radiator. The simulation setup is similar to that as shown in FIG. 2. However, instead of a liver load, a blood load 240 is used. Again, energy is fed to the antenna structure via coaxial transmission line 212.

Figure 8:
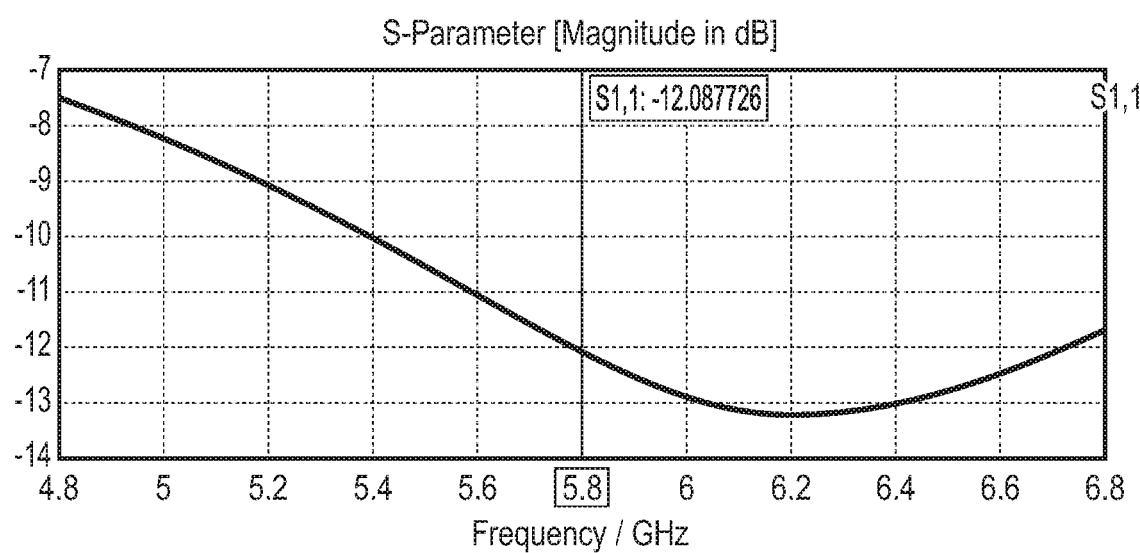
FIG. 8 is a graph showing simulated return loss for the simulation shown in FIG. 7.
Figure 9A:
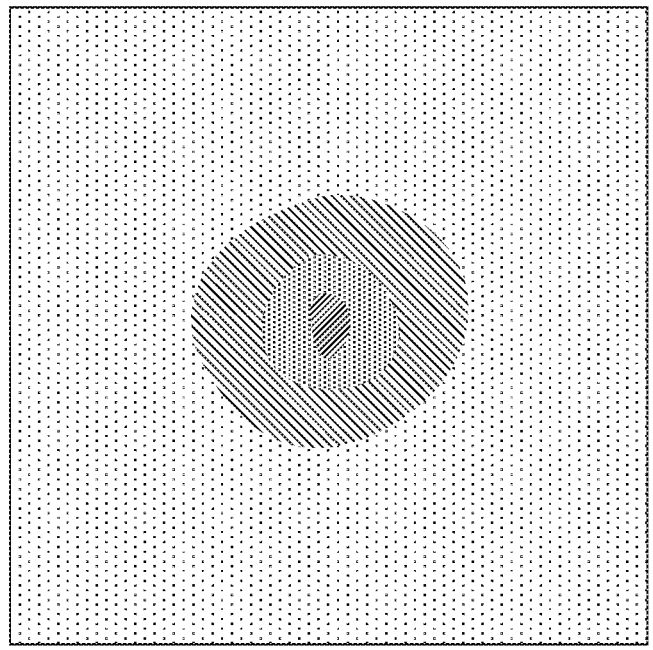
FIGS. 9A and 9B show various results of the simulation shown in FIG. 7.
Figure 9B:
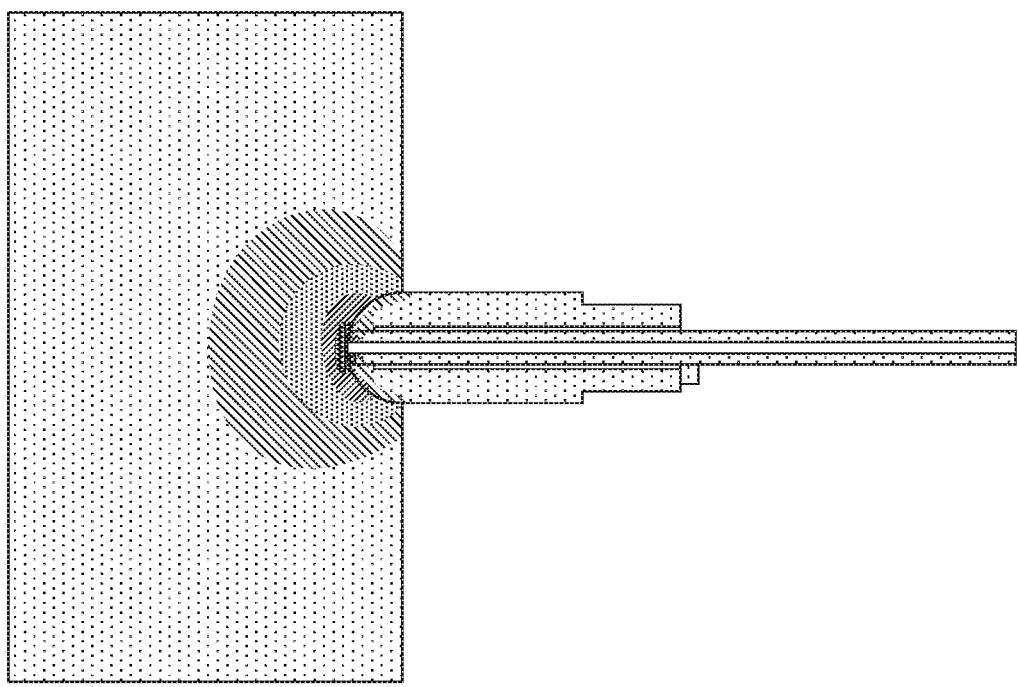
Figure 10A:
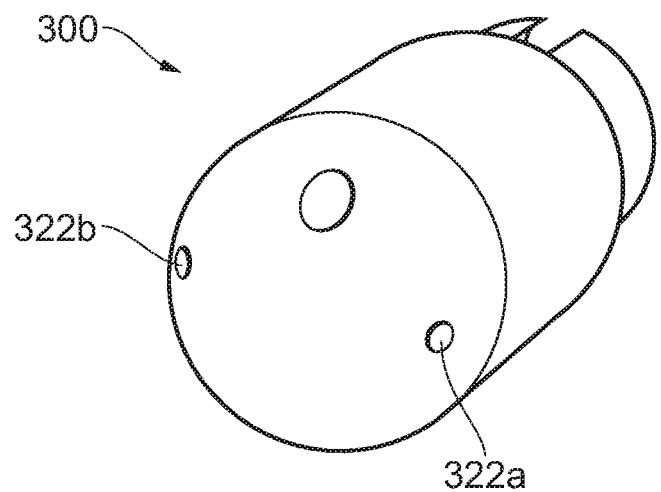
FIG. 10A is a perspective view of a dielectric body suitable for use with a helical antenna according to another embodiment of the invention.
Figure 10B:
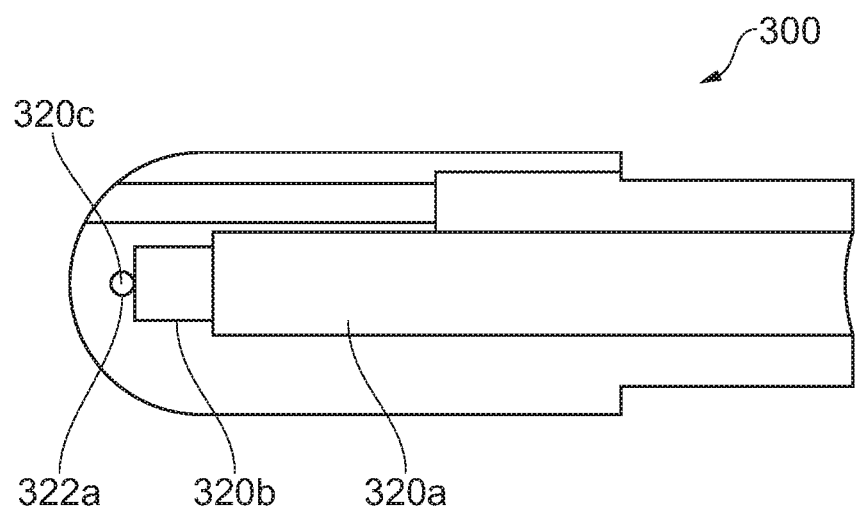
FIG. 10B is a cross-sectional view of the dielectric body shown in FIG. 10A.

FIG. 8 shows a graph of the return loss, analogous to FIGS. 3D and 5D. It should be noted that the exact form of this graph may vary depending on the position of the device relative to the blood load, e.g. on its side. It can be seen that at 5.8 GHz, the return loss is −12 08 dB. FIGS. 9A and 9B show the power loss density within the blood tissue sample immediately in front the antenna. The plots show that the power loss density is uniform, meaning that an antenna such as this would likely produce even heating/coagulation.

The invention claimed is:

1. A helical antenna structure, configured to connect to a coaxial transmission line, the coaxial transmission line having an inner conductor and an outer conductor, and the helical antenna structure having:

a dielectric support, wherein the dielectric support is substantially cylindrical and has a rounded or hemispherical portion at its distal end, wherein the rounded or hemispherical portion is dielectric;

a first helical electrode and a second helical electrode, both located on an outer surface of the dielectric support to define a helical region therebetween, the first helical electrode and second helical electrode being electrically isolated from each other;

a first connection means configured to connect the first helical electrode to the inner conductor of the coaxial transmission line;

a second connection means configured to connect the second helical electrode to the outer conductor of the coaxial transmission line;

wherein:

the dielectric support includes a channel or a chamber configured to receive the coaxial transmission line including the inner conductor and the outer conductor, such that a distal end of the inner conductor and a distal end of the outer conductor of the coaxial transmission line are located at or near the rounded or hemispherical portion at the distal end of the dielectric support;

the dielectric support is configured to embed a portion of the coaxial transmission line including the distal end of the inner conductor and the distal end of the outer conductor within the dielectric support, and the first connection means and the second connection means are located in bores through the dielectric support at or near the distal end of the dielectric support, the bores arranged to connect, respectively, the first helical electrode to a distal end of the inner conductor, and the second helical electrode to a distal end of the outer conductor;

at least one of the first helical electrode and the second helical electrode is configured to act as a radiating antenna structure for outwardly emitting a microwave frequency or radiofrequency (RF) field; and the first helical electrode and the second helical electrode are configured to sustain an electric field in the helical region therebetween.

2. The helical antenna structure according to claim 1, wherein the dielectric support has a channel running there through, from the proximal end to the distal end, the channel terminating in an aperture.

3. The helical antenna structure according to claim 2, further including a retractable needle slidable mounted in the channel.

4. The helical antenna according to claim 2, wherein the dielectric support comprises a plurality of holes between the channel and an outer surface thereof, the holes being arranged to permit gas to flow between the electrodes.

5. The helical antenna according to claim 2, wherein the channel is arranged to convey liquid.

6. The helical antenna according to claim 5, wherein the liquid is adrenaline.

7. The helical antenna structure according to claim 1, wherein the first helical electrode and the second helical electrode have the same pitch.

8. The helical antenna structure according to claim 7, wherein the first helical electrode is located diametrically opposite the second helical electrode.

9. A helical antenna structure, configured to connect to a coaxial transmission line, the coaxial transmission line having an inner conductor and an outer conductor, and the helical antenna structure having:

a dielectric support, wherein the dielectric support is substantially cylindrical and has a rounded distal end, or a hemispherical portion at its distal end;

a first helical electrode and a second helical electrode, both located on an outer surface of the dielectric support, and electrically isolated from each other;

a first connection means for connecting the first helical electrode to the inner conductor of the coaxial transmission line;

a waveguide or transmission line structure for conveying microwave frequency or radiofrequency (RF) energy from a proximal end to a distal end of the helical antenna structure to connect the first helical electrode and the second helical electrode to the coaxial transmission line;

wherein:

at least one of the first helical electrode and the second helical electrode is configured to act as a radiating antenna structure for outwardly emitting a microwave frequency or radiofrequency (RF) field;

the first helical electrode and the second helical electrode are configured to sustain an electric field in the helical region therebetween;

the waveguide or transmission line structure is in the form of a third helical electrode together with the first helical electrode, the third helical electrode being located beneath the outer surface of the dielectric support or embedded within the dielectric support and configured to be connected to the outer conductor of a coaxial transmission line at a feed point at a proximal end of the third helical electrode, wherein a distal end of the second helical electrode is electrically connected to a distal end of the third helical electrode by a conducting member.

10. The helical antenna structure according to claim 9, wherein the third helical electrode follows the same helical path as the first helical electrode, and is located radially inwards therefrom.

11. The helical antenna structure according to claim 10, wherein the first helical electrode, and the third helical electrode are made from strips of conducting material, such that the first helical electrode and the third helical electrode form a microstrip line.

12. The helical antenna structure according to claim 11, wherein the first helical electrode is at least three times wider than the third helical electrode.

13. The helical antenna structure according to claim 9, wherein the dielectric support has a channel running there through, from the proximal end to the distal end, the channel terminating in an aperture.

14. The helical antenna structure according to claim 13, further including a retractable needle slidable mounted in the channel.

15. The helical antenna according to claim 13, wherein the dielectric support comprises a plurality of holes between the channel and an outer surface thereof, the holes being arranged to permit gas to flow between the electrodes.

16. The helical antenna according to claim 13, wherein the channel is arranged to convey liquid.

17. The helical antenna according to claim 16, wherein the liquid is adrenaline.

* * * * *